(12) United States Patent
Huetter et al.

(10) Patent No.: US 8,208,132 B2
(45) Date of Patent: Jun. 26, 2012

(54) CONDENSATION NUCLEUS COUNTER

(75) Inventors: Christian R. Huetter, Brodingberg (AT); Helmut Pongratz, Graz (AT); Alexander Bergmann, Graz (AT)

(73) Assignee: AVL List GmbH, Graz (AT)

( * ) Notice: Subject to any disclaimer, the term of this patent is extended or adjusted under 35 U.S.C. 154(b) by 283 days.

(21) Appl. No.: 12/656,027

(22) Filed: Jan. 13, 2010

(65) Prior Publication Data
US 2010/0180666 A1  Jul. 22, 2010

(30) Foreign Application Priority Data
Jan. 19, 2009  (AT) ............... GM25/2009 U

(51) Int. Cl.
*G01N 15/10* (2006.01)
(52) U.S. Cl. ........................................ 356/37
(58) Field of Classification Search ........ 356/37
See application file for complete search history.

(56) References Cited

U.S. PATENT DOCUMENTS

| | | | |
|---|---|---|---|
| 4,790,650 A | 12/1988 | Keady | |
| 5,239,356 A | 8/1993 | Hollander et al. | |
| 5,992,216 A * | 11/1999 | Wang et al. | 73/28.01 |
| 6,498,641 B1 * | 12/2002 | Schildmeyer | 356/37 |
| 6,829,044 B2 | 12/2004 | Liu | |
| 7,724,368 B2 | 5/2010 | Ahn | |
| 7,975,564 B2 * | 7/2011 | Ulevicius et al. | 73/863 |

FOREIGN PATENT DOCUMENTS
GB  1422188  1/1976
* cited by examiner

*Primary Examiner* — Lisa Caputo
*Assistant Examiner* — Punam Roy
(74) *Attorney, Agent, or Firm* — Dykema Gossett

(57) ABSTRACT

A reservoir (4) for the working fluid of the saturation unit (3) is connected with a sampling section (1) by a pressure equalization line (9) of the gas that is loaded with solid particles, as a result of which a sucking back of the working fluid from the reservoir (4) into the sampling section (1) and other sections of the measurement environment that are connected with such are prevented, even in the presence of unfavorable pressure conditions.

2 Claims, 1 Drawing Sheet

CONDENSATION NUCLEUS COUNTER

BACKGROUND OF THE INVENTION

1. Field of the Invention

The invention concerns a condensation nucleus counter with a heated saturation unit through which gas flows that is loaded with solid particles from a sampling section supplied by a supply line that has a porous saturation element, which heated saturation unit is supplied with working fluid from an attached reservoir, a condensation unit that is downstream of a saturation unit, as well as a particle counter that is downstream of the condensation unit.

2. The Prior Art

Units of the type mentioned are known, for example, from the German utility model 73 21 827 or also from U.S. Pat. No. 4,790,650 and are used for measuring or counting very small particles by their effect on the dispersion of light in a ray of light. But these effects are then not safely or easily verifiable and measurable in the event the solid particles have dimensions that are too small (typically less than 0.3 pm), which is the case especially, for example, for the solid particles in exhaust gas of combustion engines and specifically diesel engines, which are almost exclusively responsible for corresponding analyses of the harmfulness of these exhaust gases.

In order to now also be able to work with particle counters of the type mentioned for particle sizes below the safe or simple limits of detection. It has become known, for example, from the named publications, to enlarge the apparent diameter of the particulate material thereby, that a working fluid is permitted to condense onto their surface, as a result of which easy and safe counting is possible in the desired manner, which is representative for the type and number of the particulate material in the particle-loaded gas flow. Aside from the use of, for example, water or water vapor as working fluid, for the improvement or optimization of the condensing, various other working fluid are common or have been analyzed—for example, alcohols and the indicated analyses of the exhaust gases of combustion engines, preferably also butanol. But working fluids of this type are not without problems for many applications with respect to their composition or their chemical components, as a contamination connected with certain operating conditions of such measurement units (especially fluctuating pressure conditions, pressure pulses) could, up to now, not be precluded with certainty by using other measuring methods or device sections, and local measurement errors connected with such must be avoided at all costs.

It is the problem of the present invention to improve a measuring unit of the type described at the beginning in such a way that its use is possible in all areas of environmental conditions that usually occur without disadvantageously influencing the other measurement environment.

SUMMARY OF THE INVENTION

This problem is solved by a condensation nucleus counter of the type mentioned at the beginning thereby, that the reservoir for the working fluid of the saturation unit is connected with the sampling section of the gas that is loaded with solid particles by a pressure equalization line. In this surprisingly simple manner, it can now be prevented with certainty that pressure fluctuations or pressure pulses can occur in the sampling section of the gas that is to be measured resulting in a back-suction of the working fluid into this section or beyond it into sections positioned behind it in the other measurement environment. It is thereby unimportant at which specific location of the sampling section this pressure equalization takes place, as this does not need to be ensured at the 100% level in order to provide the desired effect.

In the pressure equalization line, in a further preferred embodiment of the invention, a filter can be provided, preferably in the close-up range of the reservoir, which on the one hand prevents the defection of droplets of working fluid, and on the other hand the entry of solid particles from the gas flow. Naturally, a filter of this type is to be designed with as little resistance to the flow as possible, so that it does not impair the pressure equalization or the chronological progression of such.

In a further preferred embodiment of the invention, the sampling section for the gas that is loaded with solid particles has, independent of the supply line to the saturation unit, an exhaust line in which a controllable valve is located, for example, a proportional valve, as a result of which an advantageous possibility exists for setting the pressure of the sampling section and thus also the pressure of the saturation unit and the condensation unit at defined pressure conditions.

In the following, the invention is explained in more detail with the aid of examples of embodiments that are schematically shown in the drawings.

DETAILED DESCRIPTION OF THE PREFERRED EMBODIMENT

Figure 1:
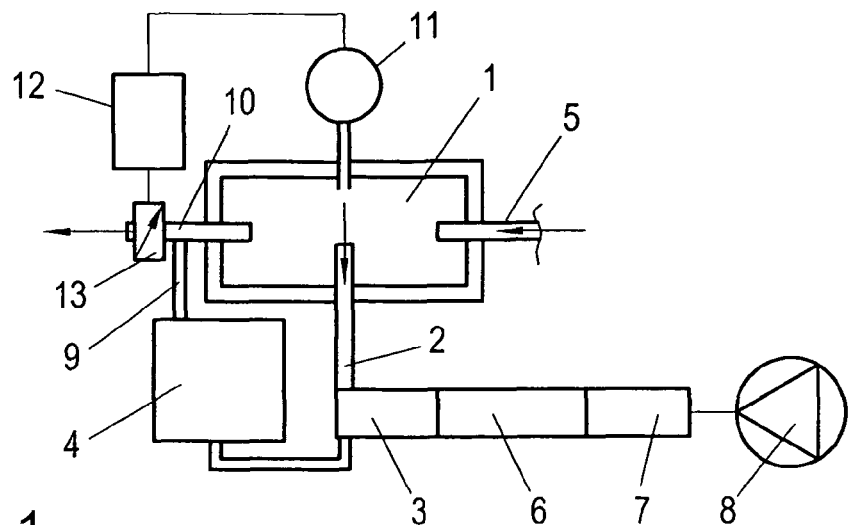
FIG. 1 shows a schematic unit of a condensation nucleus counter in accordance with the invention, and FIG. 2 a somewhat more detailed scheme of a different, corresponding unit.

The condensation nucleus counter according to FIG. 1 is provided with a heated saturation unit 3 through which gas loaded with solid particles flows from a sampling section 1 through a supply line 2, to which working fluid is supplied from a connected reservoir 4. In the stream of the gas supplied by a gas inlet 5 to sampling section 1 from a sample removal and sample preparation (not shown in detail) subsequent to saturation unit 3, (also not shown) cooled condensation unit 6 is located to which the actual particle counter 7 is connected (see FIG. 2) from which the gas is then extracted by pump 8. To ensure that even in the event of greatly fluctuating pressure conditions or pressure pulses in gas inlet 5 or in sampling section 1 the working fluid in reservoir 4 cannot be sucked back via sampling section 1 and gas inlet 5 into the remaining measurement system, the reservoir 4 is connected with sampling section 1 by a pressure equalization line 9, which according to FIG. 1 takes place at the exhaust line 10 out of the container that is limiting sampling section 1. Aside from that, the pressure equalization line 9 could also end directly in sampling section 1 or also—as shown in FIG. 2—into the supply line 2 from the (not shown in FIG. 2) sampling section to the saturation unit 3.

Further, in FIG. 1 a pressure sensor 11 at sample section 1 is also shown which works together with a control unit 12 for a proportional valve 13, as a result of which the sampling section 1, as well as the supply line 2 and the saturation unit 3 including the condensation unit 6, can be maintained at a defined level of pressure.

Figure 2:
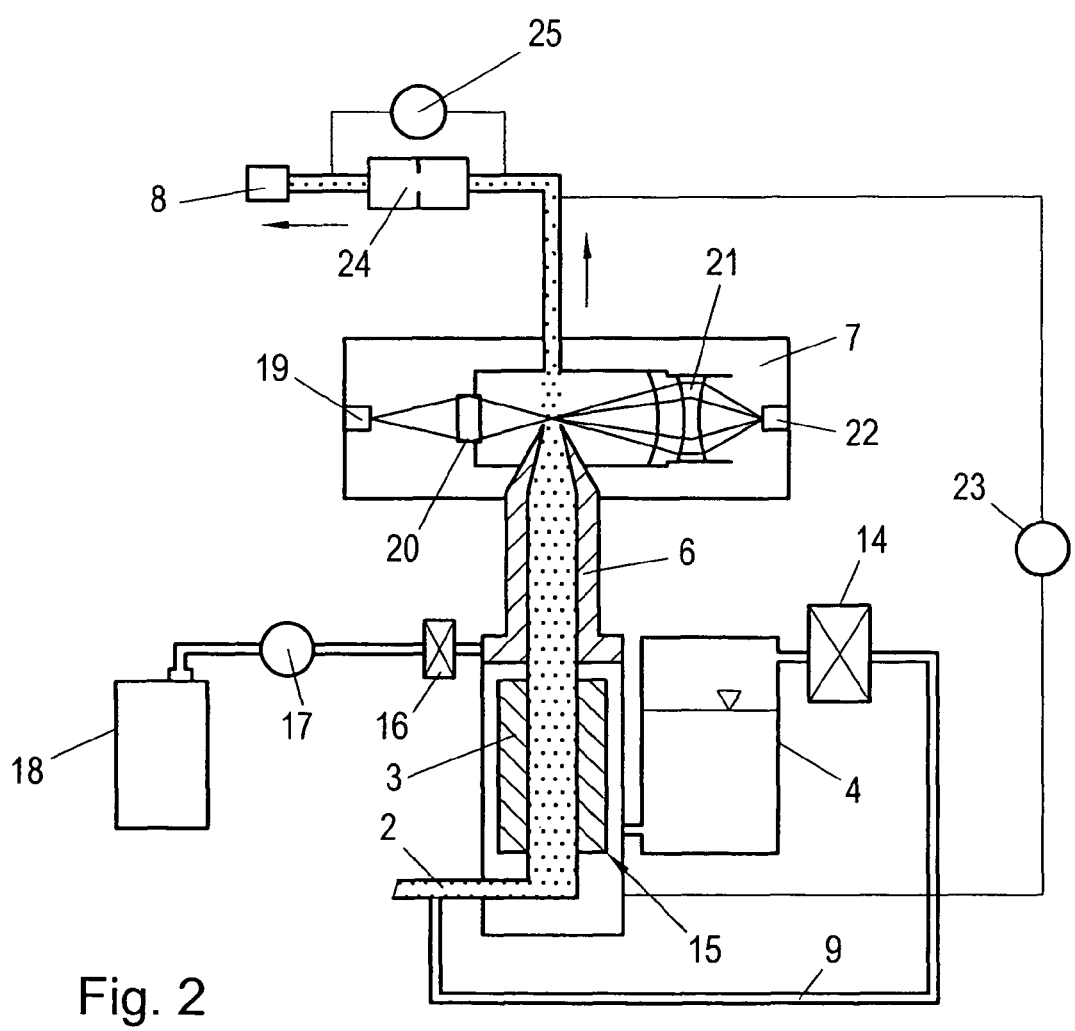

According to FIG. 2, as per the functions of the unit in FIG. 1, corresponding construction components are labeled with the same reference numbers—the above functional description of the unit as per FIG. 1 also essentially applies to FIG. 2. In addition, it can also be seen in FIG. 2, that in the pressure equalization line 9 in the close-up range of reservoir 4, a filter 14 is used, which on the one hand prevents the entry of particle-loaded gas from the supply line 2 into the reservoir 4 and on the other hand, the exit of even the smallest amount of droplet-shaped working fluid from the reservoir 4 in the direction of supply line 2. Additionally, it can also be seen that the saturation unit 3 contains a porous saturation element 15, through which particle-loaded gas flows and which is thereby moistened by working fluid, for example, 1-butanol or the like. Out of the cooled condensation unit 6, by means of a filter 16 and a pump 17, water is recycled into a receiving container 18. Possibly dripping working fluid goes back directly into the saturation unit 3.

The particle counter 7 schematically shows a laser diode 19, the light of which is focused by a focusing unit 20 at point of exit of the particle-loaded gas flow and collected by a collector 21 is directed to a detector 22. Thus, given the prerequisite of a corresponding pre-dilution of the particle-loaded gas flow, as well as a corresponding size of particles that have been artificially enlarged by the condensed working fluid—each individual particle can be determined and counted and thus the total concentration can be determined.

By means of a pressure sensor 23, the flow conditions can be measured and together with a discriminating screen 24, plus an additional pressure sensor 25, the flow can be specified or regulated by pump 8.

The invention claimed is:

1. A condensation nucleus counter which comprises:

a sampling section, a reservoir for working fluid, a heated saturation unit connected by a supply line to said sampling section and through which gas flows that is loaded with solid particles from said sampling section, said heat saturation unit including a porous saturation element to which working fluid is supplied from said reservoir, a condensation unit downstream of said heated saturation unit, a particle counter downstream of said condensation unit, and a pressure equalization line containing a filter connected between said reservoir and said sampling section.

2. A condensation nucleus counter which comprises:

a sampling section, a reservoir for working fluid, a heated saturation unit connected by a supply line to said sampling section and through which gas flows that is loaded with solid particles from said sampling section, said heat saturation unit including a porous saturation element to which working fluid is supplied from said reservoir, a condensation unit downstream of said heated saturation unit, a particle counter downstream of said condensation unit, and a particle counter downstream of said condensation unit, and an exhaust line having a controllable valve connected to said sampling section.

* * * * *